(12) United States Patent
Tai

(10) Patent No.: US 6,861,073 B2
(45) Date of Patent: Mar. 1, 2005

(54) DYSFUNCTIONAL SATIETY CENTER SYNDROME AND METHOD OF TREATMENT THEREFOR

(76) Inventor: Paul Ling Tai, 421 Glazier Rd., Chelsea, MI (US) 48127

( * ) Notice: Subject to any disclaimer, the term of this patent is extended or adjusted under 35 U.S.C. 154(b) by 138 days.

(21) Appl. No.: 10/411,786

(22) Filed: Apr. 11, 2003

(65) Prior Publication Data

US 2004/0202727 A1 Oct. 14, 2004

(51) Int. Cl.$^7$ .................................................. A61K 9/14
(52) U.S. Cl. ........................ 424/489; 424/400; 424/600; 424/682; 424/687; 514/167; 514/474; 514/909
(58) Field of Search ................................ 424/400, 489, 424/600, 682, 687; 514/167, 474, 909

(56) References Cited

U.S. PATENT DOCUMENTS

| | | | |
|---|---|---|---|
| 5,215,750 A | * | 6/1993 | Keane, II ..................... 424/440 |
| 6,447,818 B1 | | 9/2002 | Stankov ....................... 424/752 |
| 6,475,530 B1 | | 11/2002 | Kuhrts ......................... 424/725 |
| 2004/0121783 A1 | * | 6/2004 | Chua et al. ............... 455/456.1 |

* cited by examiner

Primary Examiner—Gary Kunz
Assistant Examiner—Konata M. George
(74) Attorney, Agent, or Firm—L.C. Begin & Associates, PLLC

(57) ABSTRACT

The present invention provides a method of treating obesity in mammals, particularly humans. The method comprises the step of administering a dietary supplement that includes about 25 mg to about 10 g calcium carbonate precipitate; about 25 mg to about 10 g coral calcium; about 10 mg to about 10 g magnesium carbonate; about 10 mg to about 5 g potassium carbonate; a plurality of vitamins, including Vitamin C; and a plurality of amino acids.

12 Claims, No Drawings

DYSFUNCTIONAL SATIETY CENTER SYNDROME AND METHOD OF TREATMENT THEREFOR

TECHNICAL FIELD

The present invention relates generally to formulations for assisting in weight control in mammals, for example humans, and more particularly to such a formulation that is a composition containing measured proportions of a plurality of vitamins and minerals.

BACKGROUND OF THE INVENTION

Understanding and facilitating weight control has represented a personal challenge for many individuals throughout much of modern history. As a public health matter, the health science community has long sought dietary, pharmaceutical, herbal and other effective means for assisting people in achieving and maintaining a healthy body composition. In the Western World, the proportion of the population that is overweight has increased dramatically over the last century. Estimates place approximately 30 percent of the adult American population as obese, defined as having a body weight of 30 percent or more above an ideal body weight. In addition, the sheer percentage of overweight adults has climbed to approximately 65 percent of the total population. This condition has now reached epidemic proportions. It is strongly believed that the problems in the West with obesity, and weight control generally, are largely the result of diet. The term "Western Diet" has come to be used to describe the diet typical of many Americans. This type of diet is high in sugar, high in fat, in particular animal fats, and includes only relatively low amounts of fiber and fruits and vegetables. In contrast, Asian diets are believed to be superior. The typical Asian diet is lower in sugar and fat, and higher in fiber and fruits and vegetables. As an example of the significance of the difference in diet, Asian populations tend to have a dramatically lower incidence of obesity and other weight problems. However, many people of Asian descent that conform their dietary habits to American norms develop weight-related problems similar to many Americans. It is believed that the Western Diet results in a relatively high concentration of free radicals in the body. Thus, free radicals have been at least loosely associated with different forms of cancer, aging and other ailments. In addition, free radicals throughout the body are eliminated by pairing their free electrons with electrons otherwise present in the nervous system, blood, or elsewhere in the body. Thus, free radicals may be said to "steal" electrons useful or essential in numerous other physiological functions.

Innumerable "miracle diets," herbs, drugs and other techniques have been proposed over the years for assisting in bringing this scourge under control. Among the more popular plans have been diet drugs, for example, stimulants containing caffeine or amphetamine derivatives. The drug cocktail known by the trade name "Phen-Fen" offered promise in the 1990's as an effective pharmaceutical treatment, however, its use was linked to heart valve damage, and it was pulled from the shelves. Other popular recent formulations have included "blockers," compounds that claim to adsorb or otherwise attach to and allow elimination of fats, sugars, etc. without metabolism by the body. Even if these formulations are effective in assisting in weight control, they present a significant drawback in that they also block essential nutrients and/or essential fats. Moreover, many fats are actually nutritious, and are an integral part of a healthy diet.

In addition to the ingestion of pharmaceutical and herbal compounds, various food-type diets have been proposed. Perhaps most familiar of these is the "Adkins Diet." The Adkins diet is characterized by ingestion of relatively high amounts of fatty and protein-rich foods, absent any significant consumption of carbohydrates, including fruits and vegetables. The efficacy of the Adkins diet has been seriously called into question. Further, high fat diets have been shown to be associated with a higher incidence of heart disease, cancer, strokes and a host of other health problems.

A more traditional approach has been the calorie counting diet. However, it is well known that restricting calorie and food intake creates substantial cravings for the foods that an individual is denied. For instance, upon losing weight via a calorie-reduced diet, individuals often binge, returning to their old eating habits with a vengeance. For example, rather than eating a single slice of pizza after finishing a calorie restricted diet, individuals may fail to achieve satisfaction until they have gorged themselves on an entire pizza. A very common, repeating pattern of weight loss and weight gain, known as "yo-yo-ing" is observed in many persons attempting to lose weight on such a diet. Not only are calorie-restricted diets of limited long-term effectiveness, they can create feelings of unpleasantness for the individuals following them. Typically, individuals feel a significant deprivation of the pleasure and satisfaction associated with eating.

A technical term well known in the health sciences for the state of satisfaction an individual reaches after completing a meal is "satiety." This term, satiety, represents an essentially homeostatic state wherein the individual "feels" that their cravings are satisfied or minimized. Many physiological factors are believed to bear on an individual's satiety. For instance, gustation, or taste, olfaction, or smell, as well as a feeling of fullness of the stomach may all contribute to whether an individual feels "sated."

The present invention is directed to one or more problems or shortcomings set forth above, and otherwise well known in the health sciences.

SUMMARY OF THE INVENTION

It is an object of the present invention to provide a formulation for assisting in weight control.

It is a further object of the present invention to provide a formulation useful in eliminating excess free radicals in a physiological environment.

In one aspect, the present invention provides a method for treating obesity in mammals. The method includes the step of administering a dietary supplement comprising about 25 mg to about 10 g calcium carbonate precipitate; about 25 mg to about 10 g coral calcium; about 10 mg to about 10 g magnesium carbonate; about 10 mg to about 5 g potassium carbonate; about 25 mg to about 10 g vitamin C; a plurality of vitamins; a plurality of amino acids.

DETAILED DESCRIPTION OF PREFERRED EMBODIMENTS

In one aspect, the present invention comprises a neutraceutical formulation useful in treating obesity in humans. As used herein, "neutraceutical" refers to a class of compositions used as nutritional supplements, or otherwise as materials that are ingested for their healthfull benefits, and are generally free from manufactured pharmaceuticals. The formulation contains the ingredients set forth in Table 1. All of the components are preferably used, and may be present in amounts anywhere within the disclosed ranges.

TABLE 1

| Component | Low Amount | High Amount | Preferred Amount |
|---|---|---|---|
| Vitamin C | 25 mg | 10,000 mg | 2,245 mg |
| Calcium Carbonate Precipitate | 25 mg | 10,000 mg | 600 mg |
| Coral Calcium | 10 mg | 10,000 mg | 500 mg |
| Magnesium Carbonate | 10 mg | 10,000 mg | 1,000 mg |
| Potassium Carbonate | 10 mg | 5,000 mg | 5,000 mg |
| Vitamin D | 0.01 mg | 150 mg | 0.10 mg |
| Vitamin B6 | 1 mg | 250 mg | 10 mg |
| Boron Citrate | 1 mg | 100 mg | 25 mg |
| L-Glutamine | 5 mg | 1,000 mg | 60 mg |
| Lysine | 1 mg | 1,000 mg | 20 mg |
| Methionine | 0.5 mg | 500 mg | 5 mg |
| Threonine | 0.5 mg | 500 mg | 5 mg |
| Valine | 1 mg | 1,000 mg | 10 mg |
| Leucine | 1 mg | 1,000 mg | 15 mg |
| Isoleucine | 1 mg | 1,000 mg | 10 mg |
| Histioline | 0.5 mg | 500 mg | 5 mg |
| L-Carnitine | 10 mg | 2,500 mg | 250 mg |

In a preferred embodiment, compositions according to the present invention are produced in a powdered form. It should be appreciated, however, that tablets, liquid slurries or other formulations might be concocted without departing from the scope of the present invention. Various food colorings or flavorings, such as natural or artificial fruit flavorings, or sweeteners may be added to the powdered composition. It is believed that the effective amounts of the composition range from a low end of approximately ¼ teaspoon taken once a day to a high end, of approximately 1 teaspoon taken up to about five times a day.

The dosage amounts will vary depending on the ultimate body composition goals of persons taking the formulation, as well as the actual body size and weight of the person. The duration of treatment is dependent upon the amount of weight that a person wishes to lose. Thus, treatment duration can range anywhere from a few days to several months or even years. It is even contemplated that many individuals will wish to incorporate the treatment program into their long term weight control plans, and thus may take the product for many years. In a typical treatment program, the participant can take the formulation via any suitable means, however, it is preferred to mix the powder with water, and drink the solution/suspension, or sprinkle the powder over food.

It is believed that the mode of action of the present invention involves reducing the presence of excess free radicals in the body. The Western Diet is typified by excessive amounts of sugars and fats. The combination of these excesses with a low intake of fiber, as well as other nutrients found in fruits and vegetables, is considered to create an excess of free radicals in the body. Free radicals are widely believed to be involved in deleterious physiological phenomena. Many biochemical reactions render reaction products having unpaired electrons, known as free radicals. Most free radicals are highly reactive, and their creation can initiate free radical chain reactions, whereby the radical (having an unpaired electron) product of one reaction becomes the starting material for another reaction. Thus, free radical reactions can continue to form in a long causal chain, eventually involving physiological materials that are damaged or otherwise altered by their involvement in the free radical chain reaction. It is believed that ubiquitous free radical chain reactions in the human body, prevalent in persons following the Western Diet pattern of eating, consume electrons otherwise available to perform critical physiological functions. In other words, the excess free radicals eat up electrons that the body's cells need for healthy functioning. In particular, it is believed that healthy neurological and endocrine (hormonal) functioning can be compromised when excess free radicals deplete the availability of free electrons in body tissues, causing disruptions in the stability and/or availability of bio-compounds, cell walls, and tissues.

During the last several years, significant progress has been made in understanding the neuronal networks and hormonal systems that underlie the interaction between the brain and the enteric nervous system. However, the genetic and molecular mechanisms that control these interactions remain to be elucidated. It is hypothesized that a heretofore unknown receptor system may be involved. One ligand thought to be associated with such a system is an acylated peptide hormone called ghrelin. Grehlin is known to be produced in relatively large quantities from previously unrecognized endocrine-like cells ("grehlin cells") in the digestive system. Ghrelin levels are believed to be associated with proper human growth hormone secretion, and also believed to be associated with upper gastrointestinal (GI) tract motility. Very little is yet known of the origin or development of ghrelin cells or their likely relationship with cells of the enteric nervous system. However, a connection between grehlin concentrations and satiety is proposed herein, and forms the technological basis for the present invention.

As a person consumes food, various body systems become involved in the sensation and perception of fullness and satisfaction. In particular, it is believed that the function of a region of the brain, referred to herein as the "satiety center," is critical in communicating to the rest of the body that a person has consumed enough food to satisfy their physiological needs. The nervous system structures that are considered to make up the satiety center include the limbic system, arcuate nucleus, and the third ventricle of the hypothalamus at the hippocampal foundation. At least one study has indicated that one of the strongest predictors of a person being overweight is recognizing their own satiety. See, "*Appetite For Destruction*", *Elle Fitness News*, November 2002.

In normal function, a person consumes food, and a signal, hypothesized to be a "neuro-endocrine signal," is sent to the satiety center of the brain. As used herein, the term neuro-endocrine signal should be taken to mean electrical signals communicated via the nervous system that are associated with hormone levels. For example, many different physiological conditions or states are considered to result from, or be associated with hormone levels in the body. The level of certain hormones is in turn considered to be associated with certain nervous system functions. As hormone levels go up or down in the digestive system, proximate nerve cells are hypothesized to increase or decrease their rate of firing; or alternatively, a greater or lesser number of nerve cells fires per unit time. In either case, the pattern of electrical signals sent from the digestive system to the brain is affected by the presence or absence of certain hormones, or the absolute levels of the hormones in the digestive system. The brain responds to this communication from the digestive system by sending electrical signals to other parts of the body that are involved in satiety. These parts of the body may include parts of the digestive system, sensory organs such as the nose and tongue, etc.

It is believed that an important element in the satiety signaling system is the physiological connection between cells lining the stomach, and the satiety center of the brain. High concentrations of grehlin are believed to impart various "feeding urges" to the person. These can include, for example, appetite changes, smell and taste changes, and changes in the sense of fullness. Thus, in general, the hungrier a person is, the higher their levels of grehlin in the stomach. When a person begins eating, the grehlin-producing cells lessen grehlin production, and grehlin levels drop off accordingly. It is believed that lower grehlin levels are associated with satiety, or a feeling of satisfaction. The hypothesis for how this is achieved involves a system analogous to a neuro-endocrine wire connecting the stomach with the satiety center of the brain. As grehlin levels drop in the stomach, other cells of the stomach epithelial lining begin to produce a biochemical known as cholecystokinin. The increasing level of cholecystokinin is believed to result in electrical signaling being sent from the stomach to the satiety center of the brain via the nervous system. This signaling may be induced by the rise of cholecystokinin levels, the drop in grehlin levels, or a combination of both. The electrical signaling in turn induces the satiety center to send electrical signals via the nervous system to the various physical areas associated with the sensation and perception of satiety and/or fullness.

Proper neurological signaling is necessary for the above-described system to function properly. Because electrical and neurotransmitter signals are facilitated by electrons, sufficient bio-available electrons are necessary for appropriate communication between the cells of the stomach and the satiety center of the brain, as well as for communication within the various structures comprising the satiety center. Moreover, bio-availability of electrons is believed to be crucial in appropriate signaling from the satiety center to the various physiological regions involved in satiety generally. As described, the excess of free radicals associated with the Western Diet is believed to reduce the quantity of bio-available electrons, inhibiting proper functioning of the satiety center and its communication with the stomach. Because proper neuro-endocrine communication is thereby disrupted, the satiety center does not activate the various physical centers, like taste, smell, digestive system to let the person recognize the point at which they should stop eating. Stated another way, the person does not know when their hunger has been satisfied.

The present invention comprises a plurality of electron-donating ionic minerals and other substances, combined in specific proportions. By administering regular doses of these healthful vitamins and minerals in the prescribed dosage and with the appropriate frequency, electron deficiency resulting from the Western Diet can be remedied. Consequently, it is believed that the functioning of the satiety center and neural communication in general can be improved, enhancing a person's capacity for recognizing when they should stop eating. One example of how the present invention is believed to accomplish this goal is demonstrated by the change in oxidation reduction (ORP) potential induced by mixing a quantity of a composition according to the present invention with de-ionized water. This value is preferably measured with an instrument known as the "Milwaukee Model MSM 510 ORP Monitor," available from Flying Fish Express of Los Angeles, Calif.

In general, an oxidation reduction potential that is negative represents an excess of electrons, while an oxidation reduction potential that is positive indicates an absence of electrons. De-ionized water has an oxidation reduction potential of approximately 74 millivolts (mV). In one example of the present invention's efficacy, approximately 4 grams of a powdered composition according to a preferred formulation of the present invention were mixed with 10 ounces of water. After three minutes, the ORP of the mix was measured. The ORP reading was negative 250 mV. This represents an increase of approximately ten million electrons in the solution.

When introduced in vivo, the increase in electrons is believed to neutralize the free radicals that interfere with proper electron levels, and thereby interfere with satiety recognition, as described herein. Thus, brain functioning is improved, and the neural communication between the stomach and the satiety center is allowed to work more efficiently. In addition, the present invention includes all the essential amino acids. Based on experimentation with various formulations, it is believed that including all the amino acids in the formulation has the desired effect that the cells in the stomach that produce grehlin are "turned off" more rapidly than they would be through eating alone.

The present invention can be ingested before, during or after a meal, however, it is preferable to ingest the formulation prior to eating so that the described process can begin prior to actually eating, allowing the sensation and perception of satiety to take effect as soon as possible. While a preferred embodiment has been described, those skilled in the art will appreciate that various modifications might be made to the presently disclosed embodiments without departing from the intended spirit and scope of the present invention, defined in terms of the claims set forth below. Other aspects, features and embodiments will be apparent upon an examination of the following Examples, demonstrating the usefulness of the present invention, and the appended claims.

EXAMPLES ILLUSTRATING THE USEFULNESS OF THE INVENTION

Example I

Forty-year old male, MM,
Weight Control/Dietary History:
    Subject presents with severe craving of convenient snack food all day long; subject reports that cravings are more excessive late at night.
Dosage:
    One teaspoon of formulation (preferred proportions of components in Table 1) with water 3 times daily with food.
Duration of Treatment:
    Four weeks uninterrupted.
Quantitative Results:
    Starting weight of 199 pounds, losing 23.5 pounds, down to 176.5 pounds.
    Waist size starting from 36 inches down to 34 inches. Net loss of 2 inches.
Qualitative Results:
    Subject reports 50% decrease in cravings. Overall satisfaction level of 100% with the foregoing supplement program. Reports good control of eating habits and 85% attainment of his goals preset before starting the clinical study. Subject reports no side effects with the program and following supplement program makes him control his eating habits all day long.

Example II

Forty-eight year old female, CK.
Weight Control/Dietary History:
    Subject presents with severe craving for snacks and sweets. Subject reports that the craving is more severe at night and while watching TV.

Dosage:

Subject took 1 teaspoon of formulation (preferred proportions of components in Table 1) with water throughout the day.

Duration:

Four weeks uninterrupted.

Quantitative Results:

Starting weight of 128 pounds, losing 10 pounds down to 118 pounds.

Waist size starting from 30 inches to 26 inches. Net loss of 4 inches.

Qualitative Results:

Subject reports 75% decrease in cravings, reports excellent control of eating habits and 100% attainment of her goals preset before starting the clinical study. Subject reports no side effects with the program.

Example III

Forty-eight year old female, JJ

Weight Control/Dietary History:

Subject presents with history of eating a lot of everything at all different times.

Dosage:

Subject took ½ teaspoon of formulation (preferred proportions of components in Table 1) throughout the day with water for 30 days.

Quantitative Results:

Starting weight of 260 pounds, losing 15 pounds, down to 245 pounds.

Waist size starting from 64 inches to 59 inches, net loss of 5 inches.

Qualitative Results:

Subject reports 90% decrease in cravings. Reports that she is in control of food now. Attained 100% of her goal and feels healthier. Subject said formulation gave her an outlet for her cravings.

Example IV

Fifty-three year old female.

Weight Control/Dietary History:

Subject presents with history of eating meals and junk food all day. Subject reports craving for fast food, especially at night.

Dosage:

Subject took ½ teaspoon of formulation (preferred proportions of components in Table 1) with water for 30 days.

Quantitative Results:

Starting weight of 190 pounds, losing 10 pounds down to 180 pounds. Waist size starting from 40 inches to 36 inches.

Qualitative Results:

Subject reports 70% decrease in cravings. Reports that she is less guilty about food after taking the Craving Factor, feel healthier and in control of food. She is happy to know that there is a solution for her cravings.

Example V

Thirty-five year old female.

Weight Control/Dietary History:

Subject presents with history of eating everything all day. She reports she often has cravings for fast food and snacks of junk food.

Dosage:

Subject took ½ teaspoon of formulation (preferred proportions of components in Table 1) with water for 30 days.

Quantitative Results:

Starting weight of 165 pounds, losing 14 pounds down to 151 pounds.

Waist size starting from 37 inches to 34 inches, for a net loss of 3 inches.

Qualitative Results:

Subject reports 85% decrease in cravings. Subject reports that she is less guilty about food after taking the formulation, she feels healthier and in control of food. She just "Loved it".

Example VI

Fifty-year old female.

Weight Control/Dietary History:

Subject presents with a history of eating bread, chocolate chip cookies, and cashew nuts throughout the day. Subject reports a craving for cashew, pizza, cookies, ice cream and snacks all the time.

Dosage:

Subject took ¼ teaspoon of formulation (preferred proportions of components in Table 1) daily with water for 30 days.

Quantitative Results:

Starting weight of 156 pounds, losing 8 pounds down to 148 pounds. Waist size starting from 33 inches to 29 inches.

Qualitative Results:

Subject reports 80% decrease in cravings. Reports that she does not feel deprived of food after taking the formulation, and she is very satisfied that she can eat and lose weight.

What is claimed is:

1. A powdered composition for treating obesity, the composition comprising:

about 600 mg calcium carbonate precipitate;

about 500 mg coral calcium;

about 1,000 mg magnesium carbonate;

about 5000 mg potassium carbonate;

a plurality of vitamins;

a plurality of amino acids;

about 1 mg to about 100 mg boron citrate.

2. The composition of claim 1 wherein the plurality of vitamins comprises:

about 2,245 mg Vitamin C;

about 0.10 mg Vitamin D;

about 10 mg Vitamin B6.

3. The composition of claim 1 wherein the plurality of amino acids comprises:

about 60 mg of L-Glutamine;

about 20 mg of Lysine;

about 5 mg of Methionine;

about 5 mg of Threonine;

about 10 mg of Valine;

about 15 mg of Leucine;

about 10 mg of Isoleucine;

about 5 mg of Histioline;

about 250 mg of L-Carnitine.

4. A method of treating obesity in mammals by administering a dietary supplement, the dietary supplement comprising:

about 25 mg to about 10 g calcium carbonate precipitate;

about 25 mg to about 10 g coral calcium;

about 10 mg to about 10 g magnesium carbonate;

about 10 mg to about 5 g potassium carbonate;

a plurality of vitamins;

a plurality of amino acids.

5. The method of claim 4 wherein the dietary supplement comprises:
about 150 to about 600 mg calcium carbonate precipitate;
about 125 mg to about 500 mg coral calcium;
about 250 to about 1000 mg magnesium carbonate;
about 50 to about 200 mg potassium carbonate.

6. The method of claim 5 wherein:
the plurality of vitamins comprises:
about 550 mg to about 2245 mg vitamin C;
about 0.025 mg to about 10 mg Vitamin D;
about 2.5 mg to about 10 mg Vitamin B6;
and further comprising about 6.25 to about 25 mg boron citrate.

7. The method of claim 5 wherein the plurality of amino acids comprises:
about 15 mg to about 60 mg L-glutamine;
about 5 mg to about 20 mg lysine;
about 1.25 mg to about 5 mg methionine;
about 1.25 mg to about 5 mg threonine;
about 2.5 mg to about 10 mg valine;
about 3.75 mg to about 15 mg leucine;
about 2.5 mg to about 10 mg isoleucine;
about 1.25 to about 5 mg histioline;
about 62.5 to about 250 mg L-carnitine.

8. The method of claim 5 wherein the dietary supplement is administered at least once a day for about 15 to about 45 days.

9. The method of claim 5 wherein the dietary supplement is administered at least once a day for a predetermined treatment period.

10. The method of claim 5 wherein the dietary supplement is administered at least once a day for about 30 days.

11. A neutraceutical composition comprising:
about 25 mg to about 10 g calcium carbonate precipitate;
about 25 mg to about 10 g coral calcium;
about 10 mg to about 10 g magnesium carbonate;
about 10 mg to about 5 g potassium carbonate;
about 25 mg to about 10 g Vitamin C;
about 0.01 mg to about 150 mg Vitamin D;
about 1 mg to about 250 mg Vitamin B6;
about 1 mg to about 100 mg boron citrate;
about 5 mg to about 1 g L-glutamine;
about 1 mg to about 1 g lysine;
about 0.5 mg to about 500 mg methionine;
about 0.5 mg to about 500 mg threonine;
about 1 mg to about 1 g valine;
about 1 mg to about 1 g leucine;
about 1 mg to about 1 g isoleucine;
about 0.5 mg to about 500 mg histioline;
about 10 mg to about 2.5 g L-carnitine.

12. The composition of claim 11 comprising:
about 600 mg calcium carbonate precipitate;
about 500 mg coral calcium;
about 1000 mg magnesium carbonate;
about 200 mg potassium carbonate;
about 2245 mg Vitamin C;
about 0.10 mg Vitamin D;
about 10 mg Vitamin B6;
about 25 mg boron citrate;
about 60 mg L-glutamine;
about 20 mg lysine;
about 5 mg methionine;
about 5 mg threonine;
about 10 mg valine;
about 15 mg leucine;
about 10 mg isoleucine;
about 5 mg histioline;
about 250 mg L-carnitine.

* * * * *